(12) United States Patent
Furlan et al.

(10) Patent No.: US 10,590,476 B2
(45) Date of Patent: Mar. 17, 2020

(54) METHODS FOR DETERMINING THE AMOUNT OF A NUCLEIC ACID OF INTEREST IN AN UNPROCESSED SAMPLE

(71) Applicant: Roche Molecular Systems, Inc., Pleasanton, CA (US)

(72) Inventors: Alan Furlan, Zug (CH); Michael Zeder, Buchrain (CH)

(73) Assignee: Roche Molecular Systems, Inc., Pleasanton, CA (US)

( * ) Notice: Subject to any disclaimer, the term of this patent is extended or adjusted under 35 U.S.C. 154(b) by 195 days.

(21) Appl. No.: 15/711,910

(22) Filed: Sep. 21, 2017

(65) Prior Publication Data
US 2018/0135103 A1    May 17, 2018

(30) Foreign Application Priority Data

Sep. 23, 2016 (EP) .................... 16002058

(51) Int. Cl.
*C12P 19/34* (2006.01)
*C12Q 1/686* (2018.01)
*C12Q 1/6851* (2018.01)
*C12Q 1/6806* (2018.01)

(52) U.S. Cl.
CPC .......... *C12Q 1/686* (2013.01); *C12Q 1/6806* (2013.01); *C12Q 1/6851* (2013.01); *C12Q 2531/113* (2013.01)

(58) Field of Classification Search
None
See application file for complete search history.

(56) References Cited

U.S. PATENT DOCUMENTS

2013/0288237 A1\* 10/2013 Robins ................. C12Q 1/6888
435/6.11

FOREIGN PATENT DOCUMENTS

| EP | 1589116 | 10/2005 |
|---|---|---|
| EP | 2465945 | 6/2012 |
| WO | WO2004055205 | 7/2004 |

OTHER PUBLICATIONS

Hayden et al., J. Clin. Microbiol. 50: Feb. 2012 p. 337-345.
(Continued)

*Primary Examiner* — Kenneth R Horlick
(74) *Attorney, Agent, or Firm* — Pamela C. Ancona

(57) ABSTRACT

The present disclosure relates to methods for determining the amount or concentration of a nucleic acid of interest in an unprocessed sample by analyzing a processed sample and a reference sample with digital polymerase chain reaction (dPCR).

17 Claims, 6 Drawing Sheets

(56) References Cited

OTHER PUBLICATIONS

Hayden et al., J. Clin. Microbiol. 53: May 2015 p. 1500-1505.
Caliendo et al., J. Clin. Microbiol. 44, May 2006 p. 1726-32.
Dong et al., Scientific Reports 5:13174, DOI: 10.1038/srep13174 "Comparison of four digital PCR platforms for accurate quantification of DNA copy number of a certified plasmid DNA reference material".
Coudray-Meunier Coralie et al., A comparative study of digital RI-PCR and RI-qPCR for quantification of Hepatitis A virus and Norovirus in lettuce and water samples International Journal of Food and Microbiology, vol. 201, Feb. 11, 2015 (Feb. 11, 2015), pp. 17-26.
Devonshire et al., "Highly 1-15 Reproducible Absolute Quantification of *Mycobacterium tuberculosis* Complex by Digital PCR", Analytical Chemistry, vol. 87, No. 7, Apr. 7, 2015 (Apr. 7, 2015), pp. 3706-3713.
Devonshire et al., "Application of next generation qPCR and sequencing 1-15 platforms to mRNA biomarker analysis", Methods, vol. 59, No. 1, Jan. 1, 2013 (Jan. 1, 2013), pp. 89-100.
EP16002058.2 Search Report (dated 2017).

\* cited by examiner

METHODS FOR DETERMINING THE AMOUNT OF A NUCLEIC ACID OF INTEREST IN AN UNPROCESSED SAMPLE

CROSS-REFERENCE TO RELATED APPLICATIONS

The present application claims the benefit of priority under 35 U.S.C. § 119(a) of EP16002058.2, filed Sep. 23, 2016. Reference is also made to EP16183569.9, filed Aug. 10, 2016; EP16002057.4, filed Sep. 23, 2016; and EP16191425.4, filed Sep. 29, 2016; EP16400045.7, EP16191771.1, EP16400044.0; EP16191811.5, each filed September 30; EP17154811.8, filed Mar. 14, 2017; and EP17000209.1, filed Feb. 10, 2017. The disclosures of each of these applications are incorporated herein by reference in their entireties.

FIELD OF THE DISCLOSURE

The present disclosure relates to methods for determining the amount or concentration of a nucleic acid of interest in an unprocessed sample by analyzing a processed sample and a reference sample with digital polymerase chain reaction (dPCR).

BACKGROUND

For many biological, biochemical, diagnostic or therapeutic purposes, it is necessary to accurately determine the amount or concentration of a nucleic acid in a sample. For this purpose usually external and/or internal standards are used. It is assumed that the standard has the "true concentration" which is precisely known. This may not be true and can usually not be easily verified if a relatively inaccurate method such as UV absorption or real-time PCR is used. The concentration of standards often relies on a chain of calibration standards traced back to the e.g. a WHO standard, hence quantitation errors often pile up. Quantitation standards are often imprecise, because they refer to one or several secondary standards produced and stored by a company, which again refer to another standard, e.g. the WHO standard. Even if the reference chain is properly done and accurate, the final standard may have degraded or subject to a production error, which is hard to verify unless very stringent quality control is used.

Even with methods allowing for accurate quantification of a nucleic acid in a sample tested, it is usually only possible to exactly determine the concentration of the purified nucleic acid rather than the unprocessed nucleic acid in the reaction mixture which is used as input for quantification reaction. What is however of real interest, especially in medical diagnostics applications such as initial diagnosis or disease or therapy monitoring (e.g. medical decision points in minimal residual disease monitoring) is the target concentration in the primary or unprocessed sample. The amount of nucleic acid which makes its way from the primary sample (e.g. plasma from human blood) to the quantification reaction is poorly known, because of pipetting errors and the unknown efficiency of the sample preparation process.

Therefore, it is a common practice to add a quantitation standard to the primary sample to track all losses along the preparation process. However, the state of the art is to rely on the accuracy of the quantitation standard, i.e. neglecting the errors described above. Further, it is difficult and expensive to provide a suitable external standard (e.g. a commercially available standard) in a concentration which is exactly known. Moreover, it needs to be routinely verified by a chain of secondary and tertiary standards, which in turn need to be checked on a regular basis.

Accordingly, there is a need for methods of quantifying a nucleic acid of interest, which avoids the above disadvantages, particularly which does not require a standard of known concentration.

SUMMARY

The problem was solved by methods based on digital polymerase chain reaction (dPCR) in combination with a reference sample which is used in a double function. First, it is added to a dPCR run as an external standard. Secondly, the same reference sample is used as an internal standard, preferably by adding it to the primary sample. It runs through the whole sample preparation process in the same way as the nucleic acid of interest (target nucleic acid). Both the internal and the external reference are quantified using dPCR. The ratio of internal vs external reference quantification gives the yield of the sample preparation prior to the dPCR. Knowing this yield, the initial target concentration in the primary sample can be calculated. The reference used with dPCR leads to a full understanding of standards used in dPCR and helps preventing miscalculation due to pipetting and dilution errors. Even with non-precise standards, the absolute accuracy of dPCR is further improved and standards may be re-calibrated as a bonus.

Thus, the disclosure provides a method for determining the amount or concentration of a nucleic acid of interest in an unprocessed sample, the method comprising the steps of:
 a) providing an unprocessed sample suspected of containing the nucleic acid of interest and a reference sample known to contain a reference nucleic acid, which is different from the nucleic acid of interest;
 b) combining the unprocessed sample with a defined amount of the reference sample, thereby obtaining a combined sample;
 c) processing the combined sample, thereby obtaining a processed sample suitable for digital polymerase chain reaction (dPCR);
 d) performing dPCR with the processed sample, thereby determining the amount or concentration of the nucleic acid of interest and the amount or concentration of the reference nucleic acid in the processed sample;
 e) performing the dPCR with a defined amount of the reference sample, thereby determining the amount or concentration of the reference nucleic acid in the defined amount of the reference sample;
 f) comparing the amount or concentration of the reference nucleic acid determined in step d) to that determined in step e), thereby determining the yield of the nucleic acid in step c); and
 g) determining the amount or concentration of the nucleic acid of interest in the unprocessed sample based on the amount or concentration of the nucleic acid of interest in the processed sample determined in step d) and the yield determined in step f).

In a specific embodiment, the disclosure contemplates a method for determining the amount or concentration of a nucleic acid of interest in an unprocessed sample, the method comprising the steps of:
 a) providing an unprocessed sample suspected of containing the nucleic acid of interest;
 b) providing a reference sample known to contain a reference nucleic acid, which is different from the nucleic acid of interest;

c) processing the reference sample, thereby obtaining a processed reference sample suitable for dPCR;
d) performing the dPCR with the processed reference sample, thereby determining the amount or concentration of the reference nucleic acid in the processed reference sample;
e) performing the dPCR with a defined amount of unprocessed reference sample, thereby determining the amount or concentration of the reference nucleic acid in the defined amount of the unprocessed reference sample;
f) comparing the amount or concentration of the reference nucleic acid determined in step d) to that determined in step e), thereby determining the yield of the nucleic acid in step c);
g) processing the unprocessed sample, thereby obtaining a processed sample suitable for dPCR, wherein the processing steps c) and g) are identical;
h) performing the dPCR with the processed sample, thereby determining the amount or concentration of the nucleic acid of interest; and
i) determining the amount or concentration of the nucleic acid of interest in the unprocessed sample based on the amount or concentration of the nucleic acid of interest in the processed sample determined in step i) and the yield determined in step f).

In the methods described herein, (i) the amount or concentration of the reference nucleic acid in the reference sample is compared to a reference value, thereby controlling the reference sample; (ii) the amount or concentration of the reference nucleic acid in the reference sample is unknown or not predetermined; and/or (iii) the amount or concentration of the reference sample in step e) is identical to that in step b). In addition, the reference nucleic acid has one or more of the following characteristics: (i) is a nucleic acid selected from the group consisting of DNA, cDNA, RNA and a mixture thereof; (ii) has the same primer binding site as the nucleic acid of interest; (iii) has a primer binding site different from that of the nucleic acid of interest; (iv) has a length in nucleic acids that differs from that of the nucleic acid of interest by at most 50%, at most 25%, at most 10% or at most 5%; (v) has a sequence that is at least 50% identical, at least 60%, at least 70% or at least 80% identical to that of the nucleic acid of interest; (vi) has a content of G and C that differs from that of the nucleic acid of interest by at most 50%, at most 25%, at most 10% or at most 5%; and (vii) comprises a part that is not part of the nucleic acid of interest and that is used for detecting the reference nucleic acid.

Moreover, the nucleic acid of interest has one or more of the following characteristics: (i) is a nucleic acid selected from the group consisting of DNA, cDNA, RNA and a mixture thereof; (ii) comprises a part that is not part of the reference nucleic acid and that is used for detecting the nucleic acid of interest; and (iii) is indicative of a microorganism, a cell, a virus, a bacterium, a fungus, a mammal species, a genetic status or a disease.

Still further, the unprocessed sample has one or more of the following characteristics: (i) has been obtained from a cell culture, a source suspected of being contaminated or a subject, particularly wherein the subject is selected from the group consisting of a human, an animal and a plant, especially a human; and (ii) is selected from the group consisting of a body fluid, blood, blood plasma, blood serum, urine, bile, cerebrospinal fluid, a swab, a clinical specimen, an organ sample and a tissue sample.

The processing step can include one or more of the following processes: dilution, lysis, centrifugation, extraction, precipitation, filtration, and purification.

In a particular embodiment, dPCR, as used herein, is characterized by one or more of the following: (i) is carried out in a liquid, in a gel, in an emulsion, in a droplet, in a microarray of miniaturized chambers, in a chamber of a microfluidic device, in a microwell plate, on a chip, in a capillary, on a nucleic acid binding surface or on a bead, especially in a microarray or on a chip; (ii) is carried out identically in at least 100 reaction areas, particularly at least 1,000 reaction areas, especially at least 5,000 reaction areas; and (iii) is carried out identically in at least 10,000 reaction areas, particularly at least 50,000 reaction areas, especially at least 100,000 reaction areas. More specifically, steps d) and e) are carried out in the same dPCR run and/or on the same dPCR device.

In a further embodiment, dPCR, as used herein comprises using one or more fluorescent probes, alone or in combination with a quencher, to detect the nucleic acid of interest and/or the reference nucleic acid. In a specific embodiment, the fluorescent probe comprises fluorescein, rhodamine, or cyanine. In this embodiment, the determining step comprises detecting a fluorescent signal.

The methods described herein can also include the use of an external control.

In a specific embodiment, the method is used to diagnose the presence or absence of a disease, a pathogen, a rare genetic sequence, a rare mutation, a copy number variation or relative gene expression. Optionally, the method is used to monitor disease progression, therapeutic response, and combinations thereof.

Figure 1:
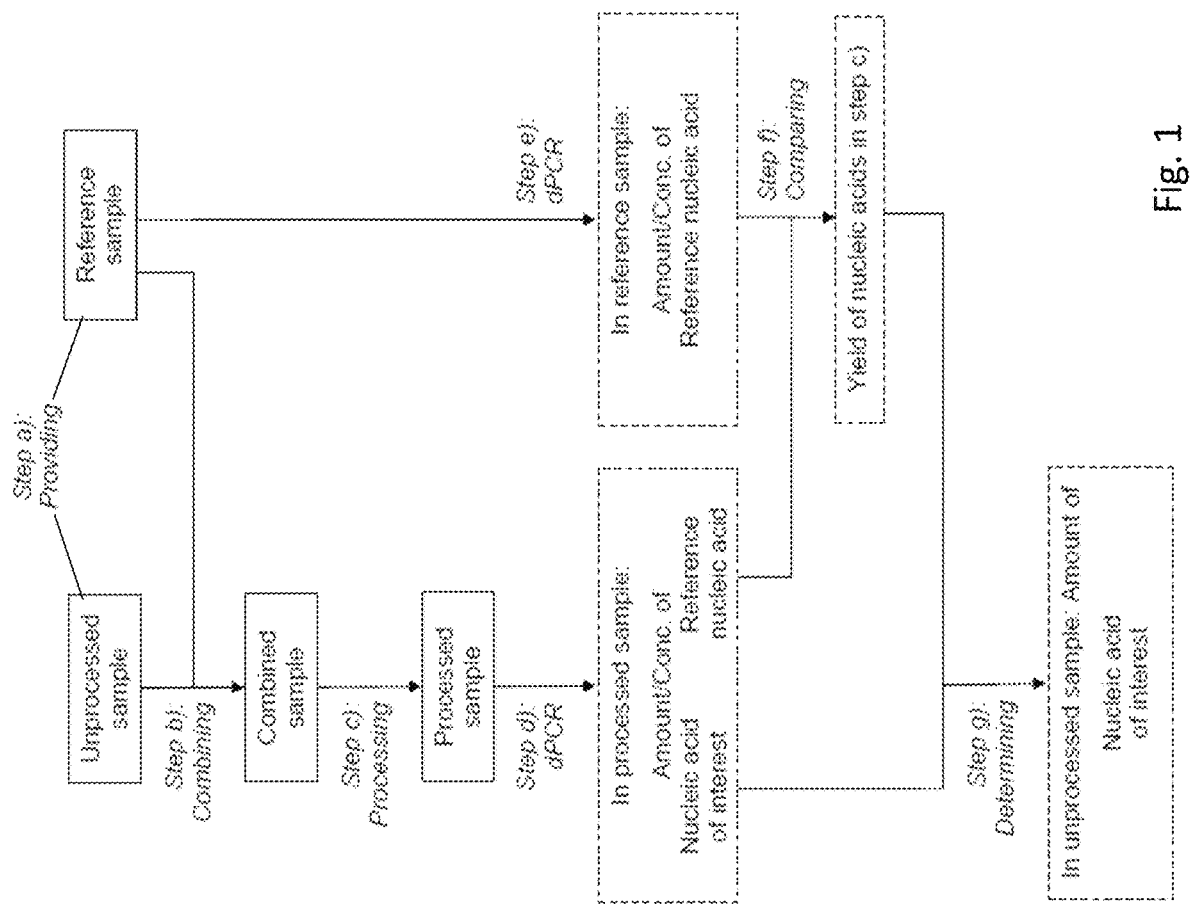
FIG. 1 illustrates the method for determining the amount or concentration of a nucleic acid of interest in an unprocessed sample according to the first aspect of the present disclosure.

$N_0(s)$: Copy number of unprocessed sample
$N_0(r)$: Copy number in reference sample η: Yield of sample preparation process
κ: Fraction of eluate introduced into PCR reaction mix

DETAILED DESCRIPTION

The present disclosure provides not only a highly accurate method to quantify a nucleic add in an unprocessed sample, but also establishes a home-made quantitation standard.

The Examples demonstrate that using the methods of the prior art one cannot precisely and accurately quantify a nucleic acid of interest (see Table 1 and Example 2). Moreover, it could be shown that the methods of the present disclosure provide more reliable results, when quantifying a nucleic acid in a sample (Example 3).

Accordingly, a first aspect the present disclosure relates to a method for determining the amount or concentration of a nucleic acid of interest in an unprocessed sample, the method comprising the steps of:
 a) providing
  an unprocessed sample suspected of containing the nucleic acid of interest and
  a reference sample known to contain a reference nucleic acid, which is different from the nucleic acid of interest;
 b) combining the unprocessed sample with a defined amount of the reference sample, thereby obtaining a combined sample;
 c) processing the combined sample, thereby obtaining a processed sample suitable for digital polymerase chain reaction (dPCR);
 d) performing the dPCR with the processed sample, thereby determining the amount or concentration of the nucleic acid of interest and the amount or concentration of the reference nucleic acid in the processed sample;
 e) performing the dPCR with a defined amount of the reference sample, thereby determining the amount or concentration of the reference nucleic acid in the defined amount of the reference sample;
 f) comparing the amount or concentration of the reference nucleic acid determined in step d) to that determined in step e), thereby determining the yield of the nucleic acid in step c); and
 g) determining the amount or concentration of the nucleic acid of interest in the unprocessed sample based on the amount or concentration of the nucleic acid of interest in the processed sample determined in step d) and the yield determined in step f).

In a second aspect, the present disclosure relates to a method for determining the amount or concentration of a nucleic acid of interest in an unprocessed sample, the method comprising the steps of:
 a) providing an unprocessed sample suspected of containing the nucleic acid of interest;
 b) providing a reference sample known to contain a reference nucleic acid, which is different from the nucleic acid of interest;
 c) processing the reference sample, thereby obtaining a processed reference sample suitable for dPCR;
 d) performing the dPCR with the processed reference sample, thereby determining the amount or concentration of the reference nucleic acid in the processed reference sample;
 e) performing the dPCR with a defined amount of unprocessed reference sample, thereby determining the amount or concentration of the reference nucleic acid in the defined amount of the unprocessed reference sample;
 f) comparing the amount or concentration of the reference nucleic acid determined in step d) to that determined in step e), thereby determining the yield of the nucleic acid in step c);
 g) processing the unprocessed sample, thereby obtaining a processed sample suitable for dPCR, wherein the processing steps c) and g) are identical;
 h) performing the dPCR with the processed sample, thereby determining the amount or concentration of the nucleic acid of interest; and
 i) determining the amount or concentration of the nucleic acid of interest in the unprocessed sample based on the amount or concentration of the nucleic acid of interest in the processed sample determined in step i) and the yield determined in step f).

As detailed above, a method to reliably determine the amount or concentration of a nucleic acid in an unprocessed sample is of particular relevance in several industrial applications, e.g. in the medical field. For several aspects it may not only be necessary to clarify whether or not a nucleic acid is present in the sample, but it may be required to determine—as precisely and accurately as possible—the amount or concentration of the nucleic acid in the unprocessed sample, e.g. a sample obtained from a patient or product. This might be of interest e.g. in the diagnosis of the severity of a disease or in environmental technology or quality control of products, e.g. in order to define contaminations or impurities.

With many samples, it is required to process the sample taken in order to carry out the method of detecting the nucleic acid in question. Often, an unknown amount of nucleic acid is lost during the processing. Moreover, it is usually required to dilute or concentrate the sample in preparation of the method of detecting the nucleic acid, namely for dPCR. The actual dilution or concentration may be different from the intended one, e.g. due to pipetting errors or inaccuracy.

dPCR (digital polymerase chain reaction, digital PCR or DigitalPCR) is a biotechnology refinement of conventional polymerase chain reaction methods that can be used to directly quantify and optionally clonally amplify nucleic acids including DNA, cDNA, RNA or mixtures thereof. The key difference between dPCR and traditional PCR (e.g. qPCR or RT-PCR) lies in the method of measuring nucleic acid amounts, with the former being a more precise method than PCR, though also more prone to error in the hands of inexperienced users, especially due to the required dilution(s). dPCR also carries out a single reaction within a sample, however the sample is separated into a large number of partitions or reaction areas and the reaction is carried out in each partition or reaction area individually. This separation allows a more reliable collection and sensitive measurement of nucleic acid amounts. Moreover, the method allows for accurate quantitation.

As detailed above, the dPCR sample is partitioned so that individual nucleic acid molecules within the sample are localized and concentrated within many separate regions (reaction areas). The partitioning of the sample allows to estimate the number of nucleic acids by assuming that the molecule population follows the Poisson distribution. As a result, each part will contain a negative or positive reaction ("0" or "1", respectively). After PCR amplification, nucleic acids may be quantified by counting the regions that contain PCR end-product positive reactions. In conventional PCR, the number of PCR amplification cycles is proportional to the starting copy number. dPCR, however, is not dependent on the number of amplification cycles to determine the initial sample amount, eliminating the reliance on uncertain exponential data to quantify target nucleic acids and therefore provides absolute quantification. Usually, the samples need to be processed for dPCR by e.g. diluting the sample (to obtain a concentration of nucleic acids allowing for dPCR), removing disturbing components, adding reagents required for dPCR etc.

The "unprocessed sample" in accordance with the present disclosure relates to a sample, which is not yet ready or suitable for dPCR and needs further processing before being used in dPCR. The sample processed and ready for use in dPCR is referred to as processed sample. Preferably, the unprocessed sample is the sample as obtained, e.g. from a subject. Due of technical or logistic reasons, it may be contemplated in the methods of the first aspect of the present disclosure to add the reference nucleic acid not to the sample as obtained, but at a later stage, e.g. if the sample has to be transported e.g. to a laboratory or if it has to be disrupted first. Step c) of the methods of the first aspect of the present disclosure relates to the processing of the combined sample. In accordance with this, the sample prior to step c) is referred to as unprocessed sample or combined sample (when the reference nucleic acid has already been added) and the sample obtained in step c) is referred to as processed sample. The above comments are analogously applicable to step g) of the methods of the second aspect of the present disclosure.

The sample may be any sample suspected of containing the nucleic acid in question, including a sample from a subject. A sample is a limited quantity of material which is intended to be identical to and represent a larger amount of that material(s). An act of obtaining a sample can be done by a person or automatically. Samples can be taken or provided for testing, analysis, inspection, investigation, demonstration, or trial use. Sometimes, sampling may be continuously ongoing. The sample may comprise or consist of a solid, a liquid or a gas; it may be material of some intermediate characteristics such as gel or sputum, tissue, organisms, or a combination of these. Preferably, the sample is liquid or a suspension which allows for easy distribution.

Even if a material sample is not countable as individual items, the quantity of the sample may still be describable in terms of its volume, mass, size, or other such dimensions. A solid sample can come in one or a few discrete pieces, or can be fragmented, granular, or powdered.

The sample in the present context is a quantity of material that is suspected of containing one or more nucleic acids that are to be detected or measured and quantified. As used herein, the term includes—without limitation—a specimen (e.g., a biopsy or medical specimen), a culture (e.g., microbiological culture) or an environmental sample, such as water or soil. Samples may be from a subject, such as an animal or human, they may be fluid, solid (e.g., stool), a suspension or tissue. The term "sample from a subject" includes all biological fluids, excretions and tissues isolated from any given subject. Preferably, the subject is an animal, more preferably a mammal or still more preferably a human. The sample may be obtained from all of the various families of domestic animals, as well as feral or wild animals, including, but not limited to, such animals as ungulates, bear, fish, rodents, etc.

Examples of samples include, but are not limited to, cell or tissue cultures, blood, blood serum, blood plasma, needle aspirate, urine, semen, seminal fluid, seminal plasma, prostatic fluid, excreta, tears, saliva, sweat, biopsy, ascites, cerebrospinal fluid, pleural fluid, amniotic fluid, peritoneal fluid, interstitial fluid, sputum, milk, lymph, bronchial and other lavage samples, or tissue extract samples The source of the sample may be solid tissue as from a fresh, frozen and/or preserved organ or tissue sample or biopsy or aspirate; or cells from any time in gestation or development of the subject.

The sample may contain compounds which are not naturally intermixed with the source of the sample in nature such as preservatives, anticoagulants, buffers, fixatives, nutrients, antibiotics, or the like.

As detailed above, the unprocessed sample contains a nucleic acid of interest, the amount or concentration of which is to be determined in the method of the present disclosure. The nucleic acid may be any nucleic acid, the amount of which is indicative of e.g. a condition, organism circumstances or event and may be therefore used in the detection of the same.

The nucleic acid may be indicative of a microorganism (such as a pathogen) and may be useful in the diagnosis of a disease, such as an infection. Infections may be caused by bacteria, viruses, fungi, and parasites or other nucleic acids containing objects. The pathogen may be exogenous (acquired from environmental or animal sources or from other persons) or endogenous (from the normal flora). Samples may be selected on the basis of signs and symptoms, should be representative of the disease process, and should be collected before administration of antimicrobial agents. The amount of the nucleic acid in the unprocessed sample may be indicative of the severity of the disease.

Alternatively, the nucleic acid may be indicative of a genetic disorder. A genetic disorder is a genetic problem caused by one or more abnormalities in the genome, especially a condition that is present from birth (congenital). Most genetic disorders are quite rare and affect one person in every several thousands or millions. Genetic disorders may or may not be heritable, i.e., passed down from the parents' genes. In non-heritable genetic disorders, defects may be caused by new mutations or changes to the DNA. In such cases, the defect will only be heritable if it occurs in the germ line. The same disease, such as some forms of cancer, may be caused by an inherited genetic condition in some people, by new mutations in other people, and mainly by environmental causes in still other people. Evidently, the amount of nucleic acid with mutation may be indicative of the disease state.

In the methods of the present disclosure, the amount or concentration of nucleic acids is determined. The amount of substance is a standards-defined quantity. The International System of Units (SI) defines the amount of substance to be proportional to the number of elementary entities present, with the inverse of the Avogadro constant as the proportionality constant (in units of mol). The SI unit for amount of substance is the mole. The mole is defined as the amount of substance that contains an equal number of elementary entities as there are atoms in 12 g of the isotope carbon-12. Therefore, the amount of substance of a sample is calculated as the sample mass divided by the molar mass of the substance.

The concentration of a substance is the abundancy of a constituent divided by the total volume of a mixture. Several types of mathematical description can be distinguished: mass concentration, molar concentration, number concentration, and volume concentration. The term concentration can be applied to any kind of chemical mixture, but most frequently it refers to solutes and solvents in solutions. The molar (amount) concentration has variants such as normal concentration and osmotic concentration. Preferably, the concentration is the amount of a constituent given in numbers divided by the total volume of a mixture.

The nucleic acid of interest according to the present disclosure is any nucleic acid, the amount or concentration of which is to be determined. A nucleic acid is a biopolymer essential for all known forms of life. Therefore, nucleic acids may be used as indicator for a particular organism, but also e.g. in case of mutations or naturally occurring variants, as indicator for a disease. Nucleic acids, which include DNA (deoxyribonucleic acid) and RNA (ribonucleic acid), are made from monomers known as nucleotides. Each nucleotide has three components: a 5-carbon sugar, a phosphate group, and a nitrogenous base. If the sugar is deoxyribose, the polymer is DNA. If the sugar is ribose, the polymer is RNA. Nucleic acids are among the most important biological macromolecules. They are found in abundance in all living organisms, where they function in encoding, transmitting and expressing genetic information—in other words, information is conveyed through the nucleic acid sequence, or the order of nucleotides within a DNA or RNA molecule. Experimental studies of nucleic acids constitute a major part of modern biological and medical research, and form a foundation for genome and forensic science, as well as the biotechnology and pharmaceutical industries. Accordingly, the method of the disclosure may be used in any of these fields.

In the methods of the disclosure, a reference sample is used. The reference sample may be any sample known to contain a reference nucleic acid. In the first aspect of the present disclosure, the reference nucleic acid is different from the nucleic acid of interest. In the second aspect of the present disclosure, the reference nucleic acid may be identical to or different from the nucleic acid of interest. As detailed above, the reference sample allows for the monitoring of the processing of the sample and may be used in order to control the dPCR.

The reference nucleic acid may be any nucleic acid as long as it can be detected by dPCR and—in the first aspect of the present disclosure—can be differentiated from the nucleic acid of interest in dPCR. It is evident that in the first aspect of the present disclosure the nucleic acid should be different from the nucleic acid of interest in order to allow for determination of the amount of nucleic acid of interest on the one hand and the reference nucleic acid on the other hand. In the second aspect of the present disclosure, the reference nucleic acid and the nucleic acid of interest may be identical. Additionally, the reference nucleic acid should be chosen that it can be differentiated from other nucleic acids present in the sample. The reference may be commercially available; it may be an accepted standard, such as a Quality Control Sample in accordance with the WHO Guidelines or a DNA standard provided by NIST (National Institute of Standards and Technology, USA). It may also be a self-made standard. The standard may result from the isolation of a nucleic acid from a culture or it may be generated by biotechnological or chemical means. Particularly, the reference nucleic acid may be an artificial sequence generated by chemical synthesis and/or genetic engineering. It will be appreciated that a reference sample similar to, but different from the nucleic acid in question should be generally advantageous in the monitoring of the processing of the sample and optionally in the control the dPCR.

As first step(s) of the methods of the present disclosure, the unprocessed sample suspected of containing the nucleic acid of interest and the reference sample known to contain a reference nucleic acid are provided (see steps a) (both aspects) and step b) (second aspect)). Preferably, the samples provided are in a liquid, which eases further method steps. Preferably, the volume of either or both samples is known. In the method of the first aspect, the unprocessed sample and the reference sample are then combined (see step b)), either by adding the reference sample to the unprocessed sample or vice versa.

As a next step, the sample in question (the combined sample in case of the methods of the first aspect OR the unprocessed sample and the reference sample in case of the methods of the second aspect) is processed (see steps c) (both aspects) and step g) (second aspect)). The processing may comprise a multitude of different steps and techniques, which will depend on various aspects, including the nature of the sample, the type of nucleic acid of interest and the dPCR method used. Typically, the processing includes purification steps and/or dilution or concentration steps. In the second aspect of the present disclosure, the processing of step g) is identical to that of step b), with the exception that different samples are used (unprocessed sample vs. reference sample).

Methods of purifying nucleic acids are well-known in the art and include—without limitation—homogenization, washing, centrifugation, extraction, etc.

After the sample has been obtained, it might be necessary to preserve the sample, e.g. by disruption of the sample, by adding preservatives, by freezing or drying the sample. For disruption of the sample obtained, physical force (e.g. a polytron, grinding or freezing) or chemical methods (e.g. lysis of cells) may be used. A detergent or a chaotrope may be used for homogenization. Nucleic acids may be extracted by the use of acid phenol/chloroform, filters, glass particles or chromatography (e.g. with appropriate nucleic acids as binding partner). It might be necessary to store the sample at any time of the processing (at the beginning, during and/or at the end of the processing). For this it might be necessary or suitable to add an appropriate medium, such as a buffered saline. It might be required to remove contaminants and/or nucleic acids, which are not of interest or might be disturbing. Enzymes may be used for removal of contaminants (such as a DNase, an RNase and/or a proteinase) or protection of the nucleic acid of interest (such as a DNase inhibitor or an RNase inhibitor). For inactivation of enzymes a heating step might be appropriate. Removal agents may be used in order to remove undesired components such as divalent cations ($Ca^{2+}$ and $Mg^{2+}$). Washing steps might be required to exchange media.

As detailed above, for dPCR the nucleic acid in question has to be present in an appropriate amount or concentration during the dPCR. Accordingly, appropriate dilution or concentration steps might be required. Dilution of nucleic acid is usually performed by adding a solvent (such as an appropriate medium for the steps to follow, e.g. a dPCR medium or dPCR buffer). It may be accompanied by washing steps, if e.g. removal of undesired components or concentration in order to obtain certain final concentrations should be intended or required. Concentration may be done by any enrichment procedure such as immunocapture, centrifugation, alcohol precipitation and the use of a binding matrix.

Typical steps for processing are detailed in the following: Nucleic acids to be analyzed are not free in solution within the fluid sample in question, but are located within closed structures such as for example cells or viruses. In diagnostic assays it is often the objective to identify especially pathogenic cells or viruses in fluid samples such as clinical samples. Such pathogens can e.g. comprise RNA viruses like for example Human Immunodeficiency Virus (HIV), Hepatitis C Virus (HCV), the West Nile Virus (WNV), Human Papilloma Virus (HPV), Japanese Encephalitis Virus (JEV), St. Louis Encephalitis Virus (SLEV) and others, or DNA viruses like e.g. Hepatitis B Virus (HBC), Cytomegalovirus (CMV) and others, or bacteria like e.g. *Chlamydia trachomatis* (CT), *Neisseria gonorrhoeae* (NG) and others. Therefore, the processing comprises releasing nucleic acids from their cellular and/or viral environment by lysing cells and/or viral capsids potentially present in the sample. To release the contents of cells or viral particles, they may be treated with enzymes or with chemicals to dissolve, degrade or denature the cellular walls or viral particles. Agents suitable to lyse cells and/or viral capsids or similar structures are commonly provided within a lysis buffer and may comprise one or more components selected from the group of a chaotropic agent (e.g. a guanidinium salts like guanidinium thiocyanate or guanidinium hydrochloride or guanidinium chloride or guanidinium isothiocyanate, urea, perchlorate such as e.g. potassium perchlorate, other thiocyanates or potassium iodide), a buffer (substance (e.g. a citrate buffer such as sodium citrate, but also a Tris (Tris(hydroxymethyl)-aminomethane) buffer such as Tris HCl, phosphate, N-(2-hydroxyethyl)piperazine-N'-(2-ethanesulfonic acid) (HEPES), acetate buffer), an alcohol (e.g. polydocanol) and a reducing agent (e.g. dithiothreitol (DTT) or 2-mercaptoethanol). These nucleic acid-degrading enzymes may be present. Accordingly, proteases which rapidly degrade the enzymes or unwanted proteins may be present.

As a typical next step, the nucleic acid is extracted from the complex lysis mixtures. There are several methods for the purification of nucleic acids. Particularly interesting for purification purposes is the adsorption of nucleic acids to a glass surface although other surfaces are possible. Many procedures for isolating nucleic acids from their natural environment have been proposed in recent years by the use of their binding behavior to glass surfaces. If unmodified nucleic acids are the target, a direct binding of the nucleic acids to a material with a silica surface is particular because, among other reasons, the nucleic acids do not have to be modified, and even native nucleic acids can be bound. These processes are described in detail by various documents. The procedure entails the selective binding of nucleic acids to glass surfaces in chaotropic salt solutions and separating the nucleic acids from contaminants such as agarose, proteins or cell residue. To separate the glass particles from the contaminants, the particles may be either centrifuged or fluids are drawn through glass fiber filters. The most particular magnetic glass particles and their use are described in WO 01/37291. A highly particular processing method is shown as FIG. 1 of WO 2012/013733.

Finally, the processing is finalized by adjusting the concentration of nucleic acids to that needed for dPCR.

After the processing, the sample is ready for dPCR, which is to follow in step d) and e) OR steps e) and h) of the methods of the disclosure according to the first and second aspect, respectively.

In dPCR, the nucleic acid in question is amplified and detected, where a number of individual molecules are each isolated in a separate reaction area.

Each reaction area (well, chamber, bead, emulsion, etc.) will have either a negative result, if no starting molecule is present, or a positive result for amplification and detection, if the targeted starting molecule is present. dPCR is a technique where a limiting dilution of the sample is made across a number of separate PCR reactions such that part of the reactions have no template molecules and give a negative amplification result. In counting the number of positive PCR reactions at the reaction endpoint, the individual template molecules present in the original sample one-by-one are counted. PCR-based techniques have the additional advantage of only counting molecules that can be amplified, e.g., that are relevant to the massively parallel PCR step in the sequencing workflow. In the digital PCR-based methods, one distributes the nucleic acid to be analyzed into a number of different reaction areas (such as well, beads, emulsions, gel spots, chambers in a microfluidic device, etc.). It is important that some reaction areas, but not all, contain at least one molecule. Typically, each reaction area will contain one or zero molecules. In practice, there will be a random distribution of molecules into reaction areas such as wells. In the case where a percentage of reaction areas (e.g., 80% is positive), a number of areas will contain one or more molecules (e.g., an average of 2.2 molecules per well). Statistical methods may be used to calculate the expected total number of molecules in the sample, based on the number of different reaction areas and the number of positives. This will result in a calculated amount or concentration of nucleic acids in the portion that was applied to the different reaction areas. A number of statistical methods based on sampling and probability can be used to arrive at this concentration. An example of such an analysis is given in Dube et al, arXiv:0809.1460v2 "Computation of Maximal Resolution of Copy Number Variation on a Nanofluidic Device using Digital PCR (2008)," found at arxiv.org, citation arXiv:0809.1460v2 [q-bio.GN], first uploaded on 8 Sep. 2008. The publication provides a series of equations that may be used to estimate the concentration of molecules and statistical confidence interval based on the number of reaction areas used in a digital PCR array and the number of positive results. Another example of this type of calculation may be found in U.S. Patent Application US 2009/0239308 A1.

Usually, a Poisson distribution is used to predict the digital regime where only a single DNA amplicon will occur in a randomly discretized volume reactor to favor only one DNA amplicon of interest per reaction volume. In this way, the PCR amplified signal (e.g., a fluorescence) emitted by each reactor volume is the product of only one amplicon and is isolated from all other discrete reactor volumes. Quantification is then achieved by counting how many digital reactors emit an amplified fluorescent signal corresponding to an intercalating dye or a particular DNA polymerase probe sequence. Since each reactor volume is limited to no more than a single DNA strand in the digital regime, one can correctly assume that 100% of its amplified fluorescence signal comes from only that one DNA strand and corresponding primer and probe set.

A number of methodologies for dPCR exist. For example, emulsion PCR has been used to prepare small beads with clonally amplified DNA—in essence, each bead contains one type of amplicon of dPCR. Fluorescent probe-based technologies, which can be performed on the PCR products "in situ" (i.e., in the same wells), are particularly well suited for this application. U.S. Pat. No. 6,440,705, contains a more detailed description of this amplification procedure. These amplifications may be carried out in an emulsion or gel, on a bead or in a multiwell plate.

dPCR also includes microfluidic-based technologies where channels and pumps are used to deliver molecules to a number of reaction areas. Suitable microfluidic devices are known in the art.

The dPCR is carried out essentially as a conventional PCR. The nucleic acids (reference or of interest) in a suitable medium are contacted with primers, probes and a thermostable polymerase (e.g. Taq polymerase) and thermocycled (cycles of repeated heating and cooling of the reaction for separation of strands and enzymatic replication. The medium usually contains deoxynucleotides, a buffer solution and ions (e.g. $Mg^{2+}$). The selectivity of PCR results from the use of primers that are complementary to the region targeted for amplification under specific thermal cycling conditions. The resulting amplification product is detected by use of a suitable probe, which is usually labelled, e.g. fluorescence-labelled. For mRNA-based PCR the RNA sample is first reverse-transcribed to complementary DNA (cDNA) with reverse transcriptase.

Typically, the PCR process consists of a series of temperature changes that are repeated 25 to 50 times. These cycles normally consist of three stages: the first, at around 95° C., allows the separation of the nucleic acid's double chain; the second, at a temperature of around 50 to 60° C., allows the binding of the primers with the DNA template; the third, at between 68 to 72° C., facilitates the polymerization carried out by the DNA polymerase. Due to the small size of the fragments the last step is usually omitted in this type of PCR as the enzyme is able to increase their number during the change between the alignment stage and the denaturing stage. In addition, a signal, e.g. fluorescence, is measured with a temperature of, for example, 80° C., in order to reduce the signal caused by the presence of primer dimers when a non-specific dye is used. The temperatures and the timings used depend on a wide variety of parameters, such as: the enzyme used to synthesize the DNA, the concentration of divalent ions and deoxyribonucleotides (dNTPs) in the reaction and the binding temperature of the primers.

In an embodiment, a dPCR method is provided that enables the unique ability to identify a greater number of fluorescent probe sequences (e.g., TaqMan probe sequences) by using multiple color, temporal, and intensity combinations to encode each unique probe sequence. Furthermore, less expensive non TaqMan-probe real-time PCR amplification indicators such as SYBR- or PicoGreen can be used to achieve multiplexed dPCR based on temporal cues alone, intensity cues alone, or intensity and temporal cues combined, thus distinguishing primer pairs at greater degrees with significant cost reductions. These can also be used to enhance controls and normalize results for greater accuracy if desired. The typical multiplexing limits from typical 5-plex qPCR can be increased to as much as 100-plex dPCR with limited spectral bands using fluorescent reporters.

In step f), the amount or concentration of the reference nucleic acid determined in step d) is compared to that determined in step e), thereby determining yield of the nucleic acid in step c).

In the context of the present disclosure, the yield is the amount/concentration of nucleic detected by dPCR after processing relative to that detected without processing. Accordingly, the yield is a percentage yield or fractional yield or relative yield, which serves to measure the effectiveness of processing. It is calculated by dividing the amount/concentration of nucleic detected by dPCR after processing by the amount/concentration of nucleic detected by dPCR without processing. If the concentration is used the volumes (if different) have to be taken into account. The calculation is based on the knowledge that usually nucleic acids are lost during processing of a sample and the loss has to be considered in the determination of the amount or concentration of nucleic acids in the sample. The loss may be due to the events described above. However, losses typically occur in the separation and purification of a desired product from a mixture.

As a last step of the methods of the disclosure, the amount or concentration of the nucleic acid of interest in the unprocessed sample is determined based on the amount or concentration of the nucleic acid of interest in the processed sample determined in step d) (first aspect) or h) (second aspect) and the yield determined in step f). For this, the amount or concentration of nucleic acid of interest in the processed sample is divided by the yield determined in step f). Further method steps may be considered when determining the amount or concentration of the nucleic acid of interest in the sample as originally obtained.

In a particular embodiment of the method of the second aspect of the present disclosure, performing steps a) and g) to i) is locally and/or temporally, particularly temporally, separated from performing steps b) to f).

In accordance with this, steps a) and g) to i) may be performed e.g. at a place, on a device and/or at a time other than that of steps b) to f). In one particular embodiment of the disclosure, steps b) to f) of the method may be used in order to determine the efficiency of the processing and the dPCR.

In one example, steps b) to f) may be performed in a well and reproducibly defined method resulting in the determination of the yield of the processing and dPCR. The value obtained for the yield may be used in order to determine the amount or concentration of a nucleic acid of interest in an unprocessed sample, wherein steps a) and g) to i) are performed in the same setting, i.e. using the same processing and dPCR methods, but at a different time. The value for the yield may be used for a multitude of subsequent methods including steps a) and g) to i). Thus, steps b) to f) may be used for characterizing the processing and dPCR. The relationship between the nucleic acid of step b) and that of step f) (i.e. the yield) may be in subsequent determinations of the amount or concentration of one or more nucleic acids of interest. In this method design it is important that each of the steps, particularly the processing (steps c) and g)) and the dPCR (steps d), e) and h)) are carried out in an essentially identical manner. This means that the same or at least similar devices, equipment, chemicals etc. are used in order to eliminate or at least minimize deviations in the yield. In one embodiment, method steps b) to f) are performed in advance and the resulting yield is reported and used in subsequent method steps a) and g) to i), which may be performed by another person or team and/or at another place.

In an embodiment of the methods of the present disclosure according to the first and second aspect the amount or concentration of the reference nucleic acid in the reference sample is compared to a reference value, thereby controlling the reference sample or the reference value. Alternatively, the amount or concentration of the reference nucleic acid in the reference sample is unknown or not predetermined. In accordance with this, a quantitation standard (e.g. a commercially available quantitation standard) or any other suitable sample may be used as reference nucleic add. The method may be used to verify the standard, to provide a new standard or to quantify the reference nucleic add.

In a particular embodiment of the methods of the present disclosure according to the first and second aspect the amount of the reference sample in step e) is identical to that in step b). Steps b) and e) quantify the reference nucleic acid in the originally employed in the processing and non-processing route, respectively, which are compared in order to determine the yield of the processing. Evidently, it is of advantage, if the same amount is used in both routes in order to minimize differences in both routes, e.g. caused by differences in dilution or assay design, which could have an impact on the comparison.

As detailed above, the nucleic acid (target or reference) may be any nucleic acid suitable for dPCR. The nucleic acid has to have a suitable length. It may contain non-nucleic acid components. It may be naturally occurring, chemically synthesized or biotechnological engineered. Preferably, the nucleic acid is selected from the group consisting of DNA, cDNA, RNA and a mixture thereof, or is any other type of nucleic acid. In another particular embodiment of the methods of the present disclosure according to the first and second aspect the reference nucleic acid is a nucleic acid selected from the group consisting of DNA, cDNA, RNA and a mixture thereof. Additionally or alternatively, the nucleic acid of interest is a nucleic acid selected from the group consisting of DNA, cDNA, RNA and a mixture thereof.

In order to minimize potentially disturbing differences in the processing efficiency between the nucleic acid of interest and the reference nucleic acid, it is particular that both nucleic acids share some similarity. Therefore, the reference nucleic acid may share structural features with the nucleic acid of interest.

The reference nucleic acid may preferably have the same primer binding site as the nucleic acid of interest. The primer binding site is needed for binding of the primer in order to allow for amplification during dPCR. An identical binding site may reduce variations in amplification efficiency.

Moreover, the reference nucleic acid may preferably have a length in nucleic acids that differs from that of the nucleic acid of interest by at most 50%, at most 25%, at most 10% or at most 5%. The length of the nucleic acids may be defined as sequence amplified by the PCR, e.g. the sequence between and including the forward and the reverse primer.

Additionally or alternatively, the reference nucleic acid may preferably have a sequence that is at least 50% identical, at least 60%, at least 70% or at least 80% identical to that of the nucleic acid of interest. Sequence identity is the amount of nucleic acids which match exactly between two different sequences. Hereby, gaps are usually not counted and the measurement is in general relational to the shorter of the two sequences. Methods and computer programs for determining sequence identity are well-known in the art.

Further, the reference nucleic acid may preferably have a content of G and C that differs from that of the nucleic acid of interest by at most 50%, at most 25%, at most 10% or at most 5%. The GC-content is the percentage of nitrogenous bases on a nucleic acid molecule that are either guanine or cytosine (from a possibility of four different ones, also including adenine and thymine/uracil). The GC pair is bound by three hydrogen bonds, while ATU pairs are bound by two hydrogen bonds. DNA with high GC-content is more stable than DNA with low GC-content, which might be of relevance during PCR. Moreover, the GC-content of primers is used to predict their annealing temperature to the template DNA. A higher GC-content level indicates a higher melting temperature.

However, the assay design might be that it is necessary or particular that a part of the reference nucleic acid that is not part of the nucleic acid of interest and that is used for detecting the reference nucleic acid. Additionally or alternatively, the nucleic acid of interest comprises a part that is not part of the reference nucleic acid and that is used for detecting the nucleic acid of interest. This is particularly relevant for the method of the first aspect of the disclosure, where both nucleic acids need to differ as both are present in the combined sample and are to be determined in the same dPCR. Alternatively, it might be desired that the reference nucleic acid comprises a primer binding site different from that of the nucleic acid of interest. This may be of interest, e.g. if a commercial standard or a statutory standard is (to be) used.

In order to render the reference nucleic acid similar to the nucleic acid of interest or to protect it, the reference nucleic acid may be armored nucleic acid. Since RNA is more prone to degradation than DNA due to influences such as alkaline pH, ribonucleases etc., reference nucleic acids made of RNA are preferably provided as armored particles. Armored particles such as especially armored RNA are described e.g. in EP910643. In brief, the RNA, which can be produced chemically or, preferably, heterologously e.g. by bacteria such as e.g. *E. coli*, is at least partially encapsulated in a viral coat protein. The latter confers resistance of the RNA towards external influences, in particular ribonucleases. It must be understood that DNA can also be provided as an armored particle. Both armored RNA and DNA are useful as reference nucleic acids in the context of the disclosure. In a particular embodiment, RNA control nucleic acids are armored with the MS2 coat protein in *E. coli*. In a further particular embodiment, DNA nucleic acids are armored using lambda phage GT11.

Armored nucleic acids better withstand exposure to ribonucleases and long-term storage in serum or plasma. The packaging also mimics naturally occurring viruses, permitting samples to be spiked with armored nucleic acids prior to purification and detection, allowing variables in nucleic acid isolation and detection to be monitored during the entire assay procedure.

In another particular embodiment of the methods of the present disclosure according to the first and second aspect the nucleic acid of interest is indicative of a microorganism, a virus, a bacterium, a fungus, a cell, a mammal species, a genetic status or a disease.

The methods of the disclosure are of particular interest in the medical field such as in diagnosis or in therapeutic monitoring and may be used in order to detect and/or quantify a nucleic acid of interest indicative of a specific microorganism, cell, virus, bacterium, fungus, mammal species, genetic status or a disease. In accordance with this, the methods may be used in the detection of a pathogen. A pathogen has the potential to cause a disease. Typically pathogen is used to describe an infectious agent such as a virus, bacterium, prion, a fungus, or even another microorganism. Of course, the methods of the disclosure may also be used to detect non-pathogenic microorganisms.

Exemplary pathogens include without limitation:

Bacterial: *Streptococcus, Staphylococcus, Pseudomonas, Burkholderia, Mycobacterium, Chlamydophila, Ehrlichia, Rickettsia, Salmonella, Neisseria, Brucella, Mycobacterium, Nocardia, Listeria, Francisella, Legionella*, and *Yersinia*

Viral: Adenovirus, Herpes simplex, Varicella-zoster virus, Cytomegalovirus Papillomavirus, Hepatitis B virus Hepatitis C virus, Hepatitis E virus, Poliovirus, Yellow fever virus, Dengue virus, West Nile virus, TBE virus, HIV, Influenza virus, Lassa virus, Rotavirus and Ebola virus Fungal: *Candida, Aspergillus, Cryptococcus, Histoplasma, Pneumocystis* and Stachybotrys Parasites: protozoan parasites, helminth parasites and arthropod parasites It is evident that the reliable detection and optionally quantification of a pathogen may be of high relevance in the diagnosis of the presence and severity of a disease.

The methods of the disclosure may be used in order to detect and quantify a specific cell, e.g. sub-population of cells. Examples of such cells include: cancer cells such as circulating tumor cells or circulating tumor microemboli, particular blood cells, such as B cells, T cells, eosinophils, etc. The cells may be rare cells, particularly wherein in the population the ratio of rare cells to total cells is at most 5%, preferably at most 1%, especially at most 0.1%, such as at most 0.01%. Rare cells may be in particular circulating tumor cells (CTC) and circulating tumor microemboli (CTM) in a patient's blood. Finding and quantifying 'rare' tumor cells (just a few CTCs mixed with the approximately 10 million leukocytes and 5 billion erythrocytes in 1 ml of blood) and being able to distinguish them from other cells, particularly epithelial non-tumor cells and leukocytes is of particular relevance in the early detection of cancer. These cells may be detected long before the tumor itself is detectable, which is evidently highly advantageous in the treatment of the cancerous diseases.

Cancer cells are characterized by particular markers, the nucleic acids of which may be used in the detection and quantification of the same. Examples which may be mentioned are: especially oncogenes and tumor suppressor genes such as p53, genes of the ras family erb-B2, c-myc, mdm2, c-fos, DPC4, FAP, nm23, RET, WT1, and the like, LOHs, for example with regard to p53, DCC, APC, Rb and the like and also BRCA1 and BRCA2 in hereditary tumors, microsatellite instability of MSH2, MLH1, WT1 and the like; also tumorous RNAs such as CEA, cytokeratins, e. g. CK20, BCL-2, MUC1, in particular tumor-specific splice variants hereof, MAGE3, Muc18, tyrosinase, PSA, PSM, BA46, Mage-1 and the like, or else morphogenic RNAs such as maspin, hCG, GIP, motilin, hTG, SCCA-1, AR, ER, PR, various hormones and the like. Furthermore, especially RNAs and proteins which affect the metastasizing profile, i. e. the expression of molecules involved in angiogenesis, motility, adhesion and matrix degradation such as bFGF, bFGF-R, VEGF, VEGF-Rs, such as VEGF-R1 or VEGF-R2, E-cadherin, integrins, selectins, MMPs, TIMPs, SF, SF-R and the like, the cell cycle profile or proliferation profile, such as cyclins (e. g. expression ratio of cyclins D, E and B), Ki67, p120, p21, PCNA and the like, or the apoptosis profile, such as FAS (L+R), TNF (L+R), perforin, granzyme B, BAX, bcl-2, caspase 3 and the like.

Alternative cells which may be determined by the methods of the disclosure include cardiovascular cells or vascular cells or vascular cells released by an inflammatory process or a fetal cell, e.g. a fetal cell in maternal blood, stem cells (e.g. cancerous stem cells), cells indicative of a minimal residual disease, cancer cells (e.g. leukemia cells). In this context, the method may be used for genotyping, diagnosis, prognosis, monitoring treatment etc.

The methods may also be used to detect and quantify the content of cells of a mammal species (e.g. in food control), a genetic status (e.g. when detecting or monitoring genetic disorders) or a disease (see above and below).

In still another particular embodiment of the methods of the present disclosure according to the first and second aspect the unprocessed sample
has been obtained from a cell culture, a source suspected of being contaminated or a subject, particularly wherein the subject is selected from the group consisting of a human, an animal or a plant, especially a human; and/or
is selected from the group consisting of a body fluid, blood, blood plasma, blood serum, urine, bile, cerebrospinal fluid, a swab, a clinical specimen, an organ sample and a tissue sample.

As detailed above, "sample" means a quantity of material that is suspected of containing a nucleic acid of interest that is to be quantified. As used herein, the term includes a specimen (e.g., a biopsy or medical specimen) or a culture (e.g., microbiological culture). Samples may be from a plant or animal, including human, it may be fluid, solid (e.g., stool) or tissue. Samples may include materials taken from a patient including, but not limited to cultures, blood, saliva, cerebral spinal fluid, pleural fluid, milk, lymph, sputum, semen, needle aspirates, and the like. The sample may be obtained from all of the various families of domestic animals, as well as feral or wild animals, including, but not limited to, such animals as ungulates, bear, fish, rodents, etc. In regard to a human sample or "tissue sample" or "patient sample" or "patient cell or tissue sample" or "specimen," each means a collection of similar cells or biological or biochemical compounds obtained from a tissue of a subject or patient. The source of the tissue sample may be solid tissue as from a fresh, frozen and/or preserved organ or tissue sample or biopsy or aspirate; blood or any blood constituents; bodily fluids such as cerebral spinal fluid, amniotic fluid, peritoneal fluid, or interstitial fluid; or cells from any time in gestation or development of the subject. The tissue sample may contain compounds which are not naturally intermixed with the tissue in nature such as preservatives, anticoagulants, buffers, fixatives, nutrients, antibiotics, or the like.

Yet, in another particular embodiment of the methods of the present disclosure according to the first and second aspect the processing comprises dilution, lysis, centrifugation, extraction, precipitation, filtration and/or purification. Further details on these methods for processing are given above.

In another particular embodiment of the methods of the present disclosure according to the first and second aspect the dPCR is carried out in a liquid, in a gel, in an emulsion, in a droplet, in a microarray of miniaturized chambers, in a chamber of a microfluidic device, in a microwell plate, on a chip, in a capillary, on a nucleic acid binding surface or on a bead, especially in a microarray or on a chip. There is a multitude of dPCR systems available, which may be used in the present disclosure. Commercialized digital PCR platforms include micro-well chip-based BioMark® dPCR from Fluidigm, through hole-based QuantStudio 12k flex dPCR and 3D dPCR from Life Technologies, and droplet-based ddPCR (ddPCR) QX100 and QX200 from Bio-Rad® and RainDrop from RainDance®. The microfluidic-chip-based dPCR can have up to several hundred partitions per panel. Droplet-based dPCR usually has approximately 20,000 partitioned droplets and can have up to 10,000,000 per reaction. The QuantStudio 12k dPCR performs digital PCR analysis on an OpenArray® plate which contains 64 partitions per subarray and 48 subarrays in total, equating to a total of 3072 partitions per array.

Droplet dPCR (ddPCR) is based on water-oil emulsion droplet technology. A sample is fractionated into a multitude of droplets (e.g. about 20,000) and PCR amplification of the template molecules occurs in each individual droplet. ddPCR technology uses reagents and workflows similar to those used for most standard TaqMan probe-based assays including droplet formation chemistry. Also, an intercalating dye, such as Evagreen, may be used. The massive sample partitioning is a key aspect of the ddPCR technique.

Evidently, the accuracy of determination by dPCR may be improved by using a greater number of reaction areas. One may use approximately, 100 to 200, 200 to 300, 300 to 400, 700 or more reaction areas, which are used for determining the amount or concentration in question by PCR. In a particular embodiment of the methods of the present disclosure according to the first and second aspect the dPCR is carried out identically in at least 100 reaction areas, particularly at least 1,000 reaction areas, especially at least 5,000 reaction areas. In a particular embodiment of the methods of the present disclosure according to the first and second aspect the dPCR is carried out identically in at least 10,000 reaction areas, particularly at least 50,000 reaction areas, especially at least 100,000 reaction areas.

In another particular embodiment of the methods of the present disclosure according to the first and second aspect steps d) and e) are carried out in the same dPCR run and/or on the same dPCR device, especially in the same microarray or on the same chip. Evidently, quantitation errors may be minimized, if the number of differences between the nucleic acid of interest and the reference nucleic acid is reduced. Therefore, it is highly particular, if the nucleic acid of interest and the reference nucleic acid are determined in the same reaction areas at the same time (neither locally nor timely separated).

In another particular embodiment of the methods of the present disclosure according to the first and second aspect the determining of the amount or concentration of the nucleic acid of interest and/or the amount or concentration of the reference nucleic acid is by fluorescence.

In PCR applications (such as Real Time PCR) fluorescence is often used to detect amplification products. It is usually carried out in a thermal cycler with the capacity to illuminate each sample with a beam of light of at least one specified wavelength and detect the fluorescence emitted by the excited fluorophore. The thermal cycler is also able to rapidly heat and chill samples, thereby taking advantage of the physicochemical properties of the nucleic acids and DNA polymerase.

The dPCR may involve the use of one or more fluorescent probes in order to detect the nucleic acid of interest and/or the reference nucleic acid, particularly in combination with a quencher or as molecular beacon or as a hydrolysis probe.

Often Fluorescence Resonance Energy Transfer (FRET) is detected in RT-PCR. FRET is a technique for measuring interactions between two molecules, in the present case two probes. In this technique, two different fluorescent molecules (fluorophores or labels) are genetically fused to a pair of probes suitable for the detection of a nucleic acid. The principle of FRET is based on the combined characteristics of the two labels. If a label is excited with a light of a particular wavelength (absorption frequency) its re-emits that energy at a different wavelength (the emission frequency). In FRET the first label is excited which in turn emits light having the emission frequency. If the emission peak of the first label (donor) overlaps with the excitation peak of the second label (acceptor), proximity of the two labels can be determined, since the first label transfers energy to the second label and the second label emits light at its own emission frequency. The net result is that the donor emits less energy than it normally would (since some of the energy it would radiate as light gets transferred to the acceptor instead), while the acceptor emits more light energy at its excitation frequency (because it is getting extra energy input from the donor fluorophore). Also the combination of a fluorescent dye with a quencher may be used. If the quencher is in proximity to the fluorescent dye, the emission of fluorescence is omitted. If the fluorescent moiety becomes separated from the quencher, the emission of the first fluorescent moiety can be detected after excitation with light of a suitable wavelength. Molecular beacons are hairpin shaped probes with an internally quenched fluorophore whose fluorescence is restored when they bind to a target nucleic acid sequence. If the nucleic acid to be detected is complementary to the strand in the loop, the duplex formed between the nucleic acid and the loop is more stable than that of the stem because the former duplex involves more base pairs. This causes the separation of the fluorophore and the quencher. Once the fluorophore is distanced from the quencher, illumination of the hybrid with light results in the fluorescent emission. The presence of the emission reports that the event of hybridization has occurred and hence the target nucleic acid sequence is present in the test sample. Hydrolysis probes consist of a fluorophore covalently attached to the 5'-end of the oligonucleotide probe and a quencher at the 3'-end. As long as the fluorophore and the quencher are in proximity, quenching inhibits any fluorescence signals. The probes are designed such that they anneal within a DNA region amplified by a specific set of primers. As the polymerase extends the primer and synthesizes the nascent strand, the 5' to 3' exonuclease activity of the polymerase degrades the probe that has annealed to the template. Degradation of the probe releases the fluorophore from it and breaks the close proximity to the quencher, thus relieving the quenching effect and allowing fluorescence of the fluorophore. Hence, fluorescence detected is indicative of the presence of the nucleic acid in question.

Representative donor fluorescent moieties that can be used with various acceptor fluorescent moieties in FRET technology include fluorescein, *Lucifer* Yellow, B-phycoerythrin, 9-acridineisothiocyanate, *Lucifer* Yellow VS, 4-acetamido-4'-isothiocyanatostilbene-2,2'-disulfonic acid, 7-diethylamino-3-(4'-isothiocyanatephenyl)-4-methylcoumarin, succinimdyl 1-pyrenebutyrate, and 4-acetamido-4'-isothiocyanatostilbene-2,2'-disulfonic acid derivatives. Representative acceptor fluorescent moieties, depending upon the donor fluorescent moiety used, include LC-Red 610, LC-Red 640, LC-Red 670, LC-Red 705, Cy5, Cy5.5, Lissamine rhodamine B sulfonyl chloride, tetramethyl rhodamine isothiocyanate, rhodamine×isothiocyanate, erythrosine isothiocyanate, fluorescein, diethylenetriamine pentaacetate or other chelates of Lanthanide ions (e.g., Europium, or Terbium). Donor and acceptor fluorescent moieties can be obtained, for example, from Molecular Probes (Junction City, Oreg.) or Sigma Chemical Co. (St. Louis, Mo.).

In another particular embodiment of the methods of the present disclosure according to the first and second aspect the fluorescent probe comprises fluorescein, rhodamine and/or cyanine. For example, the donor fluorescent moiety may be fluorescein and/or the acceptor fluorescent moiety may be selected from the group consisting of LC-Red 610, LC-Red 640, LC-Red 670, LC-Red 705, Cy5, and Cy5.5, preferably LC-Red 610 or LC-Red 640. More preferably the donor fluorescent moiety is fluorescein and the acceptor fluorescent moiety is LC-Red 640 or LC-Red 610.

Several different fluorophores (e.g. 6-carboxyfluorescein, acronym: FAM, or tetrachlorofluorescein, acronym: TET) and quenchers (e.g. tetramethylrhodamine, acronym: TAMRA) are available.

In another particular embodiment of the methods of the present disclosure according to the first and second aspect the method further includes the use of an external control, such as a negative control and/or a positive control. Even, though digital PCR does not require the calibration and internal controls necessary for qPCR, it might be intended or necessary to use them along with the methods of the present disclosure, e.g. in order to comply with GLP or legal requirements or to confirm liability of the assay. Negative controls may include no template controls or no enzyme controls. Positive control may be needed for the verification of negative results and the positive control reaction should contain the same components as the sample but include a template that is certain to amplify if the reaction goes as planned. This could be an external positive control, which is a separate sample containing the control template. Such external control reactions can help detect when a reaction fails due to cycler or reaction component problems or when an inhibitor is suppressing the reaction. Alternatively, one could use an internal positive control (IPC). To run a reaction with an IPC, the template and primers for the control target are included in the reaction along with those for the target of interest. The control target should of course be easily distinguished from the target of interest. In addition to having the advantage of not requiring a separate reaction, IPCs are useful because they can indicate problems that are intrinsic to the sample reaction.

In another particular embodiment of the methods of the present disclosure according to the first and second aspect the method is used in diagnosis, particularly for the detection of a disease, a pathogen, a rare genetic sequence, a rare mutation, a copy number variation or relative gene expression.

In general, PCR permits early diagnosis of diseases in a patient's sample. Accordingly, dPCR assays can be performed directly on genomic DNA samples to detect a disease or a pathogen. It is well-known that PCR allows for rapid and highly specific diagnosis of infectious diseases, including those caused by bacteria or viruses. PCR also permits identification of non-cultivatable or slow-growing microorganisms such as mycobacteria, anaerobic bacteria, or viruses from tissue culture assays and animal models. The basis for PCR diagnostic applications in microbiology is the detection of infectious agents and the discrimination of non-pathogenic from pathogenic strains by virtue of specific genes. Viral DNA can likewise be detected by PCR. The primers used must be specific to the targeted sequences in the DNA of a virus, and PCR can be used for diagnostic analyses or DNA sequencing of the viral genome. The high sensitivity of PCR permits virus detection soon after infection and even before the onset of disease. Such early detection may give physicians a significant lead time in treatment. The amount of virus ("viral load") in a patient can also be quantified by PCR-based DNA quantitation techniques. Moreover, the methods of the disclosure may be used in the diagnoses of diseases, e.g. cancer, involving a rare genetic sequence, a rare mutation, a copy number variation or relative gene expression. The discovery of rare genetic variants is accelerating. Some of these sequence variants are disease-causing any may be used in clinical diagnosis. Copy number variation is a source of genetic diversity in humans. Numerous copy number variations are being identified with various genome analyses. Copy number variation formation may occur by both recombination-based and replication-based mechanisms and de novo locus-specific mutation rates appear much higher than for SNPs. By various molecular mechanisms, including gene dosage, gene disruption, gene fusion, position effects, etc., copy number variations can be associated with complex diseases or can represent benign polymorphic variants. Also, expression profiles of one or more genes can provide information, which can be used in the diagnosis of diseases. Particularly, the presence or severity of a disease may be determined by analyzing relative gene expression.

In another particular embodiment of the methods of the present disclosure according to the first and second aspect the method is used in monitoring, particularly in monitoring of a patient, especially in therapy monitoring or determining therapy efficiency. In accordance with the above details, the methods may be used in monitoring in order to detect changes of a nucleic acid in sample obtained from a source at different times or conditions. Monitoring of diseases and pathogens allows for the identification of changes in disease status. It may be used in order to assess whether a therapy is effective at all or how efficient it was. This may include routine visits for a chronic disease to check on the progress or regress of the disease and the development of complications. It may be required to adjust treatment.

Unless defined otherwise, all technical and scientific terms and any acronyms used herein have the same meanings as commonly understood by one of ordinary skill in the art in the field of the disclosure. Definitions of common terms in molecular biology can be found in Benjamin Lewin, Genes V, published by Oxford University Press, 1994 (ISBN 0-19-854287-9); Kendrew et al. (eds.), The Encyclopedia of Molecular Biology, published by Blackwell Science Ltd., 1994 (ISBN 0-632-02182-9); and Robert A. Meyers (ed.), Molecular Biology and Biotechnology: a Comprehensive Desk Reference, published by VCH Publishers, Inc., 1995 (ISBN 1-56081-569-8).

The disclosure is not limited to the particular methodology, protocols, and reagents described herein because they may vary. Although any methods and materials similar or equivalent to those described herein can be used in the practice of the present disclosure, the particular methods, and materials are described herein. Further, the terminology used herein is for the purpose of describing particular embodiments only and is not intended to limit the scope of the present disclosure.

As used herein and in the appended claims, the singular forms "a," "an," and "the" include plural reference unless the context clearly dictates otherwise. Similarly, the words "comprise," "contain" and "encompass" are to be interpreted inclusively rather than exclusively. Similarly, the word "or" is intended to include "and" unless the context clearly indicates otherwise. The term "plurality" refers to two or more.

The following Examples are intended to illustrate various embodiments of the disclosure. As such, the specific modifications discussed are not to be construed as limitations on the scope of the disclosure. It will be apparent to the person skilled in the art that various equivalents, changes, and modifications may be made without departing from the scope of the disclosure, and it is thus to be understood that such equivalent embodiments are to be included herein.

EXAMPLES

Example 1 Comparison of Total Analytical Error of Different Methods

A qualitative comparison of the quantitation methods was conducted based on the analysis of various prior art documents (identified below) as well as new experiments. For this evaluation, typical error values for nucleic acid analysis were estimated considering the following definitions and equations:

Inaccuracy: The inaccuracy refers to the deviation of the average of a large set of measured values to the reference value. It is normally expressed relative to the reference value and given in percent. For quantitative nucleic acid tests, the reference concentration of a sample $c_0$ is given by the corresponding WHO standard. Hence the inaccuracy is expressed by: $(c_{avg} \ominus c_0)/c_0 * 100(\%)$.

Imprecision: The imprecision refers to the standard deviation of replicate measurements, expressed in percentage of the average value determined from a large set of replicates. In the case of concentration measurements: $STDEV(c)/c_{avg} * 100(\%)$.

Total (analytical) error: The total error TE expresses the deviation of a single measurement value from the reference value that will not be exceeded in 95% of all measurements. It is expressed by: TE=inaccuracy+2× imprecision.

In this Example, the total analytical error, consisting of imprecision and inaccuracy, as defined above, of two state-of-the art methods for quantitative nucleic acid tests (Table 1 a and b) was compared to the method described by the present disclosure (Table 1 d). Furthermore, the typical errors estimated in the tables below refer to sample concentrations in the range of the "medical decision point" which is regarded as most relevant from the application point of view.

Figure 5:
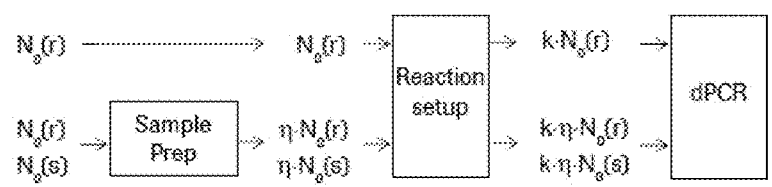
FIG. 5 shows a diagram indicating the copy numbers of the reference sample and the sample containing unprocessed and reference sample, at different stages of the process.

The following aspects were addressed:

Comparison of concentrations of reference HCV samples, determined on two nucleic acid testing systems with FDA-approved CMV monitor assays (Caliendo et al, 2006, J Clin Microbiol 44: 1726-32, referred to as Ref 1). FIG. 5 of Ref 1 shows the agreement between the Bayer bDNA and Roche RT-PCR assays (the current most widely used products for HCV viral load testing). The dotted line represents the mean difference for the samples. It can be seen that the sample-to-sample variation was large, implying an imprecision between +/−0.5 log 10 (e.g. for Genotype 2) and +/−1.0 log 10 (e.g. for Genotype 3). Furthermore, the inaccuracy (mean bias of all samples) varied between −0.1 log 10 and +0.8 log 1.

Figure 2:
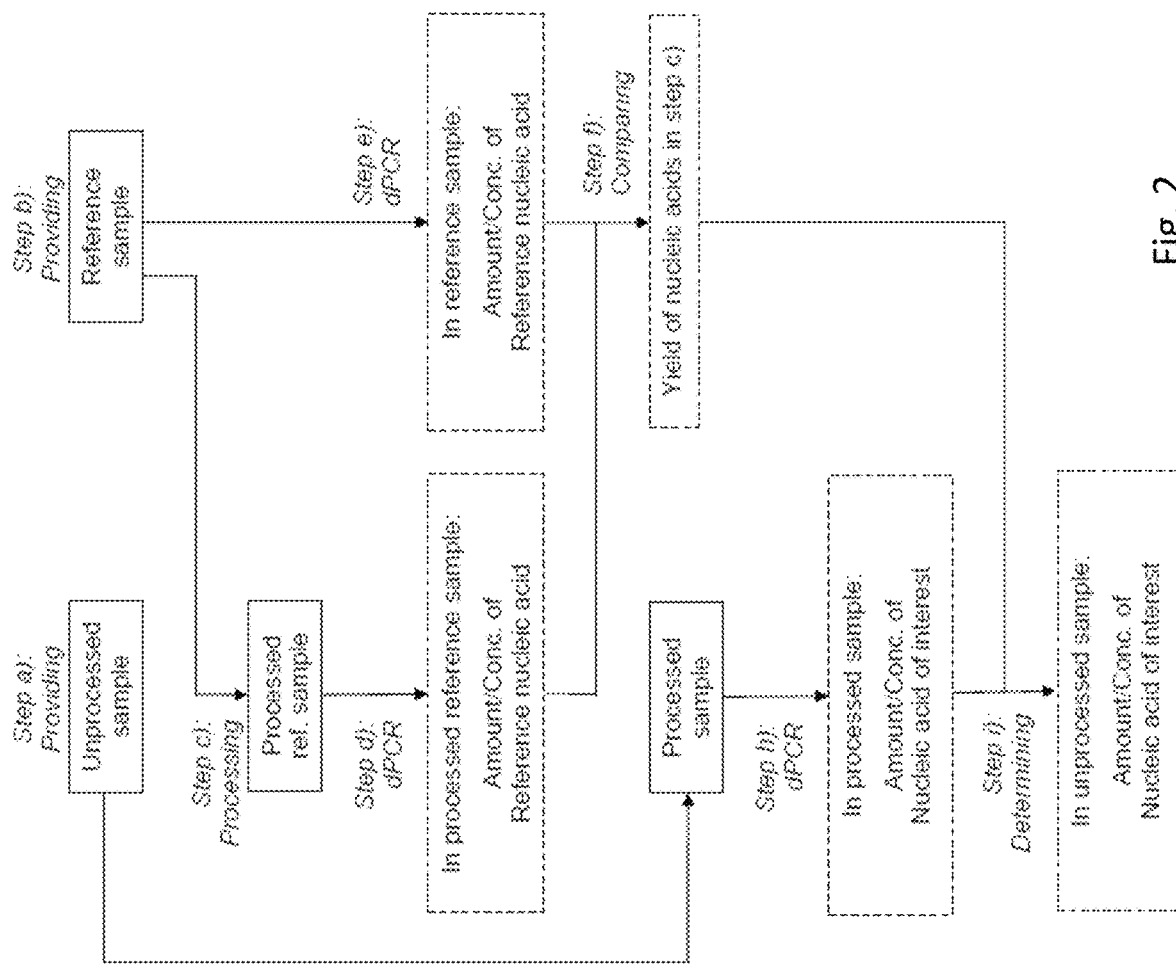
FIG. 2 illustrates the method for determining the amount or concentration of a nucleic acid of interest in an unprocessed sample according to the second aspect of the present disclosure.
Figure 3A:
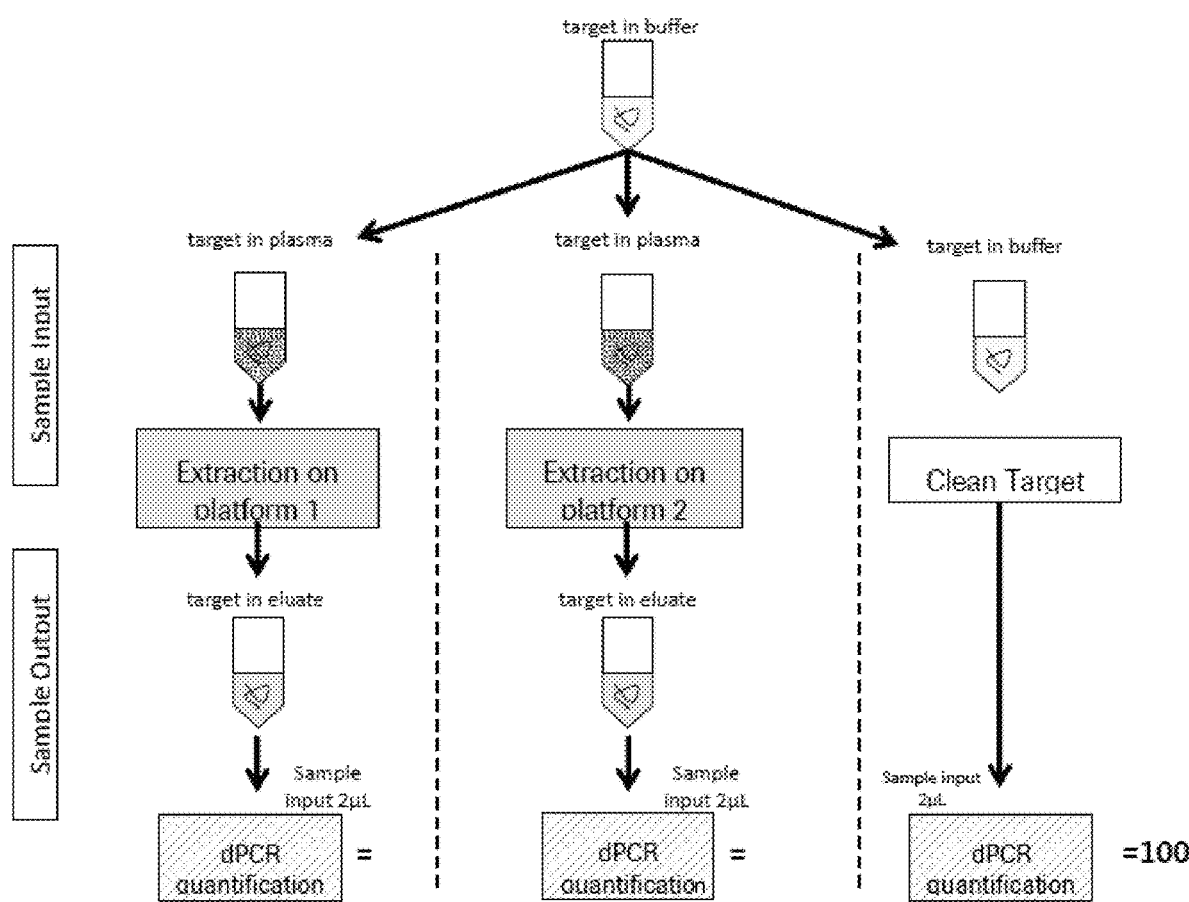
FIGS. 3A-3C illustrate the assay design for the determination of relative extraction yields (FIG. 3A), the yields of target nucleic acid (pooled sample) measured on twelve positions of extraction platform 1 (FIG. 3B), and the yields of target nucleic acid measured on twelve positions of extraction platform 2 (FIG. 3C). White and grey bars represent the data of a first and a second extraction run in FIGS. 3B-3C, respectively, carried out under the exactly same conditions. 100% yield was determined by direct quantification of the clean target using dPCR, and taking the respective dilution factors into account.
Figure 3B:
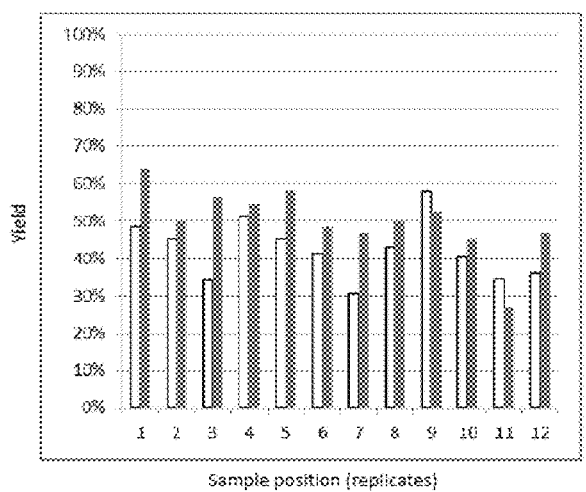
Figure 3C:
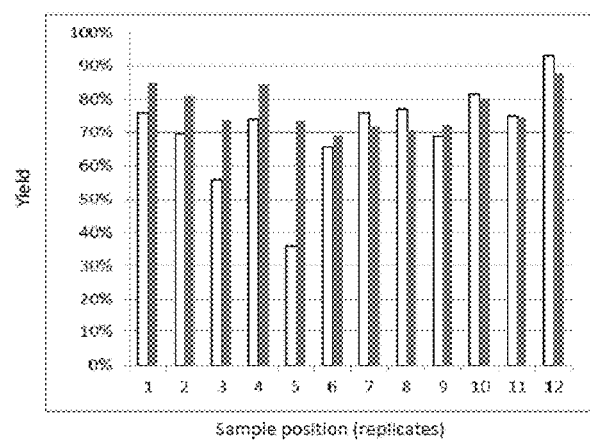

Comparison of viral loads of reference samples for CMV and EMV on different platforms with different test assays (Hayden et al., 2012, J. Clin. Microbiol. 50: 337-345, referred to as Ref 2). FIGS. 2 and 3 of Ref 2 illustrate a comparison of viral loads of reference samples for CMV and EMV on different platforms. The median titers determined on the different platforms differ by approximately a factor of ten (1 log 10 difference). The imprecision within a platform varies from a factor of 1.2 up to 10, depending on the assay and the platform.

Inaccuracy (or bias) of commercially available quantitation standards, relative to their nominal value, determined on different platforms (J. Clin. Microbial. May 2015 53:5 1500-1505, referred to as Ref 3). FIG. 1 of Ref 3 shows the inaccuracy of concentrations of common quantitation standards from different suppliers used for CMV testing, evaluated on 5 nucleic acid testing platforms. As discussed in the Ref 3, the two dPCR platforms (BioRad and Raindance) provided the most consistent and accurate results.

Typical imprecision and inaccuracy values of quantitation standards from Roche Molecular Systems (Pleasanton, Calif.), collected for each lot release. The following table (Roche data referred to as Ref 4) illustrates typical deviations between observed and assigned titer values, measured on a Roche nucleic acid testing system. In this experiment, the measured quantitation result of 8 replicates of a secondary standard was compared with the assigned titer value of 4.26 log 10. This corresponds to a concentration of 1.7*1E4 copies/ml. The mean difference was equal to the inaccuracy, while the standard deviation of the differences was equal to the imprecision of the titer value. This data was collected with a specific instrument and reagents from a specific lot. Hence the imprecision and inaccuracy values shown here do not include instrument-to-instrument variations and reagent lot-to-lot variations.

| Replicate number | Observed titer (cp/ml, log10) | Assigned titer (cp/ml, log10) | Difference (cp/ml, log10) |
| --- | --- | --- | --- |
| 1 | 4.22 | 4.26 | −0.04 |
| 2 | 4.06 | 4.26 | −0.2 |
| 3 | 4.18 | 4.26 | −0.08 |
| 4 | 4.29 | 4.26 | 0.03 |
| 5 | 4.14 | 4.26 | −0.12 |
| 6 | 4.1 | 4.26 | −0.16 |
| 7 | 4.4 | 4.26 | 0.14 |
| 8 | 4.08 | 4.26 | −0.18 |
| Mean | 4.18 | 4.26 | −0.08 |
| Stdev | 0.12 | 0.00 | 0.12 |

Comparison of dPCR quantitation results from two platforms (Roche data referred to as Ref 5). Comparison of quantitation results measured at Roche, using an experimental dPCR device (referred to hereinbelow as the "experimental dPCR system" and described in EP16183569.9; EP16002057.4; EP16191425.4; EP16400045.7; EP16191771.1; EP16400044.0, and EP16191811.5), compared to the BioRad QX100 system (BioRad. Hercules, Calif.). Imprecision of replicates ranged between 3.5 and 5%, while the mean values determined on the two platforms deviated by 2.5 and 5% for the two targets. The analysis was based on the following results:

| Target | Value | N | Bio RAD QX100 | | | N | Experimental dPCR device | | |
| --- | --- | --- | --- | --- | --- | --- | --- | --- | --- |
| | | | Valid Partitions | Positive Partitions | Copy number | | Valid Partitions | Positive Partitions | Copy number |
| FAM | Mean | 23 | 12815 | 668 | 1262 | 27 | 10568 | 1244 | 1324 |
| | STDEV | 23 | 3111 | 158 | 64 | 27 | 431 | 55 | 62 |
| | CV (%) | 23 | 24.28 | 23.62 | 5.05 | 27 | 4.08 | 4.44 | 4.66 |
| HEX | Mean | 23 | 12815 | 3055 | 6439 | 27 | 10568 | 4909 | 6601 |
| | STDEV | 23 | 3111 | 698 | 265 | 27 | 431 | 171 | 226 |
| | CV (%) | 23 | 24.28 | 22.83 | 4.11 | 27 | 4.08 | 3.48 | 3.42 |

Comparison of dPCR quantitation results from four platforms (Comparison of four digital PCR platforms for accurate quantification of DNA copy number of a certified plasmid DNA reference material, Dong et al., 2015, Scientific Reports 5: Article number: 13174, doi: 10.1038/srep13174, referred to as Ref 6). Table 1 of Ref 6 summarizes a comparison of quantitation results of four dPCR platforms. Results with linearized plasmid indicate an imprecision within a platform of 2-6%, and inaccuracies of 0-6%.

The results of the above data analysis are summarized in following Tables 1a-d.

TABLE 1a

Total error of Quantitative PCR*

| | Inaccuracy | Imprecision | Tot. error | Comment |
|---|---|---|---|---|
| Primary (WHO) standard | ±4% (±0.016log10) | ±3% (±0.012log10) | ±10% (±0.04log10) | Assuming best available quantitation methods (dPCR, cell counting, isotope dilution mass spectroscopy) |
| Secondary standard (used as reference by QS manufacturer) | ±0.2log10 | ±0.15log10 | ±0.5log10 | Dominant errors: measurement method (qPCR: e.g. thermal profile variations add inaccuracy and imprecision) and reagent instability (adds mainly inaccuracy). |
| Quantitation standard QS | ±0.3log10 | ±0.15log10 | ±0.6log10 | Error contributions: sec. standard error, lot-to-lot variation of QS (see Ref. 4), variation between platforms and kit manufacturers (see Ref. 3). |
| Target | ±0.4log10 | ±0.2log10 | ±0.8log10 | See Ref. 1 and 2 for illustrative examples. Both inaccuracy and imprecision increase due to error propagation. |

*Quantitative PCR assays rely on the accuracy and precision of the quantitation standard (QS). The quantitation standard is spiked into the primary sample (plasma sample) at a known volume and concentration. It is hence processed in the same way as the sample nucleic acid to be quantified, through the whole sample preparation step, reaction setup step and PCR. The calculation of the target concentration is done using characteristics of the real-time PCR curves of both target and quantitation standard.

TABLE 1b

Total error of dPCR using a quantitation standard QS qualified via primary and secondary standard

| | Inaccuracy | Imprecision | Tot. Error | Comment |
|---|---|---|---|---|
| Primary (WHO) standard | ±4% (±0.016log10) | ±3% (±0.012log10) | ±10% (±0.04log10) | See Table 1a |
| Secondary standard | ±0.2log10 | ±0.15log10 | ±0.5log10 | Table 1a |
| Quantitation standard QS | ±0.25log10 | ±0.02log10 | ±0.29log10 | Accuracy still relies on the calibration chain (prim/sec/QS), and is therefore only slightly improved by dPCR, while imprecision is strongly reduced. |
| Target | ±0.27log10 | ±0.03log10 | ±0.33log10 | |

TABLE 1c

Total error of digital PCR without a quantitation standard

| | Inaccuracy | Imprecision | Tot. Error | Comment |
|---|---|---|---|---|
| Target concentration in eluate | ±4% (±0.016log10) | ±3% (±0.012log10) | ±10% (±0.04log10) | Same accuracy and precision as primary standard, as quantification method is the same (dPCR). See Ref. 5 |
| Variation of sample preparation yield | ±10% (±0.04log10) | ±20% (±0.08log10) | ±50% (±0.3log10) | Sample-to-sample and system-to-system yield strongly depends on input material, reagents and process. |

TABLE 1c-continued

Total error of digital PCR without a quantitation standard

| | Inaccuracy | Imprecision | Tot. Error | Comment |
|---|---|---|---|---|
| Target concentration in eluate | ±10% (±0.04log10) | ±20% (±0.08log10) | ±50% (±0.3log10) | Main contributor to inaccuracy and imprecision is the sample prep yield |

TABLE 1d

Total error of dPCR using an in-process calibrated quantitation standard (no reference to primary and secondary standards required)

| | Inaccuracy | Imprecision | Tot. Error | Comment |
|---|---|---|---|---|
| Quantitation standard QS | ±4% (±0.016log10) | ±3% (±0.012log10) | ±10% (±0.04log10) | Same accuracy and precision as primary standard, as quantification method is the same (dPCR). See Ref. 5 and 6 |
| Target | ±6% (±0.025log10) | ±4% (±0.016log10) | ±14% (±0.057log10) | Inaccuracy and imprecision are estimated to be the root mean square of equal contributions from target and QS. |

Example 2 Determination of Relative Extraction Yields

In order to prove the accuracy of the methods of the prior art, target DNA was transferred to plasma and extracted (platform 1: Roche MagNA Pure 24 (MP24) (Roche Molecular Systems, Pleasanton, Calif.), or platform 2: Cobas® 6800 (Roche Molecular Systems, Pleasanton, Calif.)). The eluate was quantified with dPCR. The yield of target nucleic acid (pooled sample) measured on twelve positions of platform 1 and twelve positions of platform 2. Target DNA directly quantified with dPCR was set at 100%. The assay design is illustrated in FIG. 3A.

Experimental Set-Up—Platform 1:
MP24 #000503, Target: HBV EuroHep Plasmid (4.33E+05 cp/mL or 8.23E+4 IU/mL); Human EDTA Plasma (HIV/HBV/HCV negative), Sample Input Volume: 500 µL, Elution Volume: 105 µL.

Experimental Set-Up—Platform 2:
Cobas® 6800, Instrument: 1200, Reagent: Cobas® HBV Kit (Roche Molecular Systems, Pleasanton, Calif.), Target: HBV EuroHep Plasmid (4.33E+05 cp/mL or 8.23E+4 IU/mL), Human EDTA Plasma (HIV/HBV/HCV negative), Sample Input Volume: 500 µL, Elution Volume: 50 µL.

Experimental Set-Up—Experimental dPCR System:
Reagent: Master Mix (MMx) (RC09) (Roche Molecular Systems, Pleasanton, Calif.) including 100 nM TEXR as fill control, eluate from MP24/Cobas® 6800, 2 µL target per lane, Separation Fluid: PMX 200 50 cs w/o additive, experimental filling device Input Volume: 10 µL, The results are shown in FIGS. 3B (platform 2) and 3C (platform 1). White and grey bars represent the data of a first and a second extraction run, respectively, carried out under the exactly same conditions. 100% yield was determined by direct quantification of the clean target using dPCR, and taking the respective dilution factors into account. The yield can vary substantially between different platforms (e.g., about factor 2), and between positions on the same platform (e.g., up to factor of 2). Accordingly, an unknown yield introduces an error in the absolute quantification, as the yield must be known to quantify calibrators, which are in turn used to calibrate quantitation standards.

Example 3 Absolute Quantification of Primary Sample Concentration

Figure 4A:
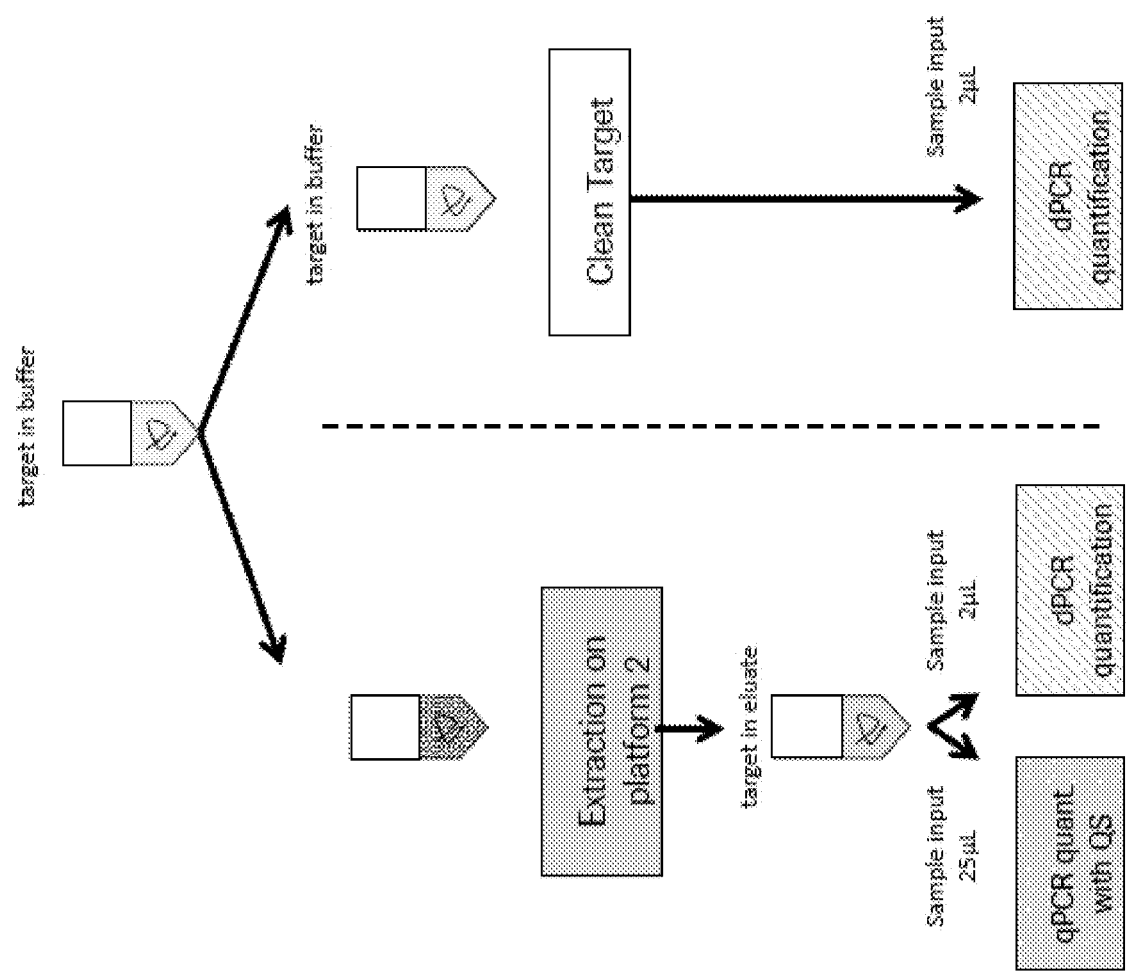
FIGS. 4A-4B illustrate the assay design for the absolute quantification of primary sample concentration (FIG. 4A) and the concentration of target in primary sample (FIG. 4B), determined on 12 positions of platform 2 and using the quantitation standard belonging to this assay. The target concentration is given relative to the concentration determined directly (w/o extraction) using dPCR.

In order to prove the improvement in accuracy of the methods of the present disclosure relative to the methods of the prior art, target DNA was transferred to plasma and extracted (platform 2: Cobas® 6800). The eluate was either quantified with qPCR (Cobas® 6800) with quantitation standard QS (state of the art) or dPCR (experimental dPCR system) including a reference nucleic acid. Target DNA directly quantified with dPCR was set at 100%. The assay design is illustrated in FIG. 4A and the experimental details are those provided in Example 2 above.

Figure 4B:
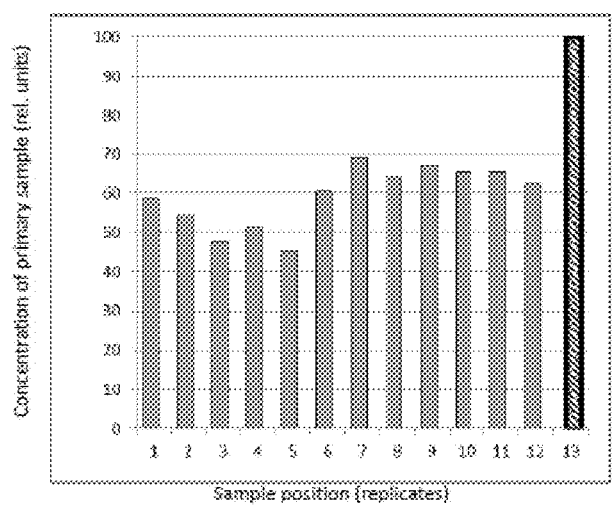

The results are shown in FIG. 4B. The concentration of target in the primary sample was determined on 12 positions of platform 2 and using the quantitation standard belonging to this assay. The target concentration is given relative to the concentration determined directly (w/o extraction) using dPCR. Note that the target nucleic acid used in this experiment is identical to the standard calibrator target used to calibrate the system for this particular assay.

The absolute quantification using a quantitation standard and qPCR can substantially deviate from the true concentration, in this case about 40% under-quantified (see columns 1 to 12 of FIG. 4B). Various explanations for this observation can be provided, including but not limited to, an incorrect quantification of the (secondary) calibrator standard or lot-to-lot variations of the quantitation standard. In contrast thereto, using the methods of the present disclosure, the concentration was correctly determined (see column 13 of FIG. 4B).

The present application is not to be limited in scope by the specific embodiments described herein. Indeed, various modifications in addition to those described herein will become apparent to those skilled in the art from the foregoing description and accompanying figures. Such modifications are intended to fall within the scope of the claims. Various publications are cited herein, the disclosures of which are incorporated by reference in their entireties.

The invention claimed is:

1. A method for determining the amount or concentration of a nucleic acid of interest in an unprocessed sample, the method comprising the steps of:
   a) providing an unprocessed sample suspected of containing the nucleic acid of interest and a reference sample known to contain a reference nucleic acid, which is different from the nucleic acid of interest;
   b) combining the unprocessed sample with a defined amount of the reference sample, thereby obtaining a combined sample;
   c) processing the combined sample, thereby obtaining a processed sample suitable for digital polymerase chain reaction (dPCR);
   d) performing dPCR with the processed sample, thereby determining the amount or concentration of the nucleic acid of interest and the amount or concentration of the reference nucleic acid in the processed sample;
   e) performing the dPCR with a defined amount of the reference sample, thereby determining the amount or concentration of the reference nucleic acid in the defined amount of the reference sample;
   f) comparing the amount or concentration of the reference nucleic acid determined in step d) to that determined in step e), thereby determining the yield of the nucleic acid in step c); and
   g) determining the amount or concentration of the nucleic acid of interest in the unprocessed sample based on the amount or concentration of the nucleic acid of interest in the processed sample determined in step d) and the yield determined in step f).

2. A method for determining the amount or concentration of a nudeic acid of interest in an unprocessed sample, the method comprising the steps of:
   a) providing an unprocessed sample suspected of containing the nudeic acid of interest;
   b) providing a reference sample known to contain a reference nucleic acid, which is different from the nucleic acid of interest;
   c) processing the reference sample, thereby obtaining a processed reference sample suitable for dPCR;
   d) performing the dPCR with the processed reference sample, thereby determining the amount or concentration of the reference nucleic acid in the processed reference sample;
   e) performing the dPCR with a defined amount of unprocessed reference sample, thereby determining the amount or concentration of the reference nucleic acid in the defined amount of the unprocessed reference sample;
   f) comparing the amount or concentration of the reference nucleic acid determined in step d) to that determined in step e), thereby determining the yield of the nucleic acid in step c);
   g) processing the unprocessed sample, thereby obtaining a processed sample suitable for dPCR, wherein the processing steps c) and g) are identical;
   h) performing the dPCR with the processed sample, thereby determining the amount or concentration of the nucleic acid of interest; and
   i) determining the amount or concentration of the nucleic acid of interest in the unprocessed sample based on the amount or concentration of the nucleic acid of interest in the processed sample determined in step h) and the yield determined in step f).

3. The method of claim 2, wherein performing steps a) and g) to i) is temporally, separated from performing steps b) to f).

4. The method of claim 1, wherein (i) the amount or concentration of the reference nucleic acid in the reference sample is compared to a reference value, thereby controlling the reference sample; (ii) the amount or concentration of the reference nucleic acid in the reference sample is unknown or not predetermined; and/or (iii) the amount or concentration of the reference sample in step e) is identical to that in step b).

5. The method of claim 1, wherein the reference nucleic acid has one or more of the following characteristics:
   (i) is a nucleic acid selected from the group consisting of DNA, cDNA, RNA and a mixture thereof;
   (ii) has the same primer binding site as the nucleic acid of interest;
   (iii) has a primer binding site different from that of the nucleic acid of interest;
   (iv) has a length in nucleic acids that differs from that of the nucleic acid of interest by at most 50%, at most 25%, at most 10% or at most 5%;
   (v) has a sequence that is at least 50% identical, at least 60%, at least 70% or at least 80% identical to that of the nucleic acid of interest;
   (vi) has a content of G and C that differs from that of the nucleic acid of interest by at most 50%, at most 25%, at most 10% or at most 5%; and
   (vii) comprises a part that is not part of the nucleic acid of interest and that is used for detecting the reference nucleic acid.

6. The method of 5, wherein the nucleic acid of interest has one or more of the following characteristics:
   (i) is a nucleic acid selected from the group consisting of DNA, cDNA, RNA and a mixture thereof;
   (ii) comprises a part that is not part of the reference nucleic acid and that is used for detecting the nucleic acid of interest; and
   (iii) is indicative of a microorganism, a cell, a virus, a bacterium, a fungus, a mammal species, a genetic status or a disease.

7. The method of claim 1, wherein the unprocessed sample has one or more of the following characteristics:
   (i) has been obtained from a cell culture, a source suspected of being contaminated or a subject, wherein the subject is selected from the group consisting of a human, an animal and a plant; and
   (ii) is selected from the group consisting of a body fluid, blood, blood plasma, blood serum, urine, bile, cerebrospinal fluid, a swab, a clinical specimen, an organ sample and a tissue sample.

8. The method of claim 1, wherein the processing step comprises one or more of the following processes: dilution, lysis, centrifugation, extraction, precipitation, filtration, and purification.

9. The method of claim 1, wherein dPCR is characterized by one or more of the following:
   (i) is carried out in a liquid, in a gel, in an emulsion, in a droplet, in a microarray of miniaturized chambers, in a chamber of a microfluidic device, in a microwell plate, on a chip, in a capillary, on a nucleic acid binding surface or on a bead;

(ii) is carried out identically in at least 100 reaction areas; and (iii) is carried out identically in at least 10,000 reaction areas.

10. The method of claim 1, wherein steps d) and e) are carried out in the same dPCR run and/or on the same dPCR device.

11. The method of claim 1, wherein dPCR comprises using one or more fluorescent probes, alone or in combination with a quencher, to detect the nucleic acid of interest and/or the reference nucleic acid.

12. The method of claim 11, wherein the fluorescent probe comprises fluorescein, rhodamine, or cyanine.

13. The method of claim 1, wherein the determining step comprises detecting a fluorescent signal.

14. The method of claim 1, wherein the method further includes the use of an external control.

15. The method of claim 1, wherein the method is used to diagnose the presence or absence of a disease, a pathogen, a rare genetic sequence, a rare mutation, a copy number variation or relative gene expression.

16. The method of claim 15 wherein the method is used to monitor disease progression, therapeutic response, and combinations thereof.

17. The method of claim 9, wherein dPCR is carried out in a droplet.

* * * * *